(12) United States Patent
Nakamura et al.

(10) Patent No.: US 12,067,807 B2
(45) Date of Patent: Aug. 20, 2024

(54) FINGERPRINT REGISTRATION METHOD AND USER TERMINAL DEVICE

(71) Applicant: PANASONIC INTELLECTUAL PROPERTY MANAGEMENT CO., LTD., Osaka (JP)

(72) Inventors: Hideyuki Nakamura, Fukuoka (JP); Ryuji Fuchikami, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/783,988

(22) PCT Filed: Dec. 11, 2020

(86) PCT No.: PCT/JP2020/046315
§ 371 (c)(1),
(2) Date: Jun. 9, 2022

(87) PCT Pub. No.: WO2021/117877
PCT Pub. Date: Jun. 17, 2021

(65) Prior Publication Data
US 2023/0009157 A1 Jan. 12, 2023

(30) Foreign Application Priority Data
Dec. 12, 2019 (JP) .................. 2019-224796

(51) Int. Cl.
*G06V 40/50* (2022.01)
*G06F 21/32* (2013.01)
(Continued)

(52) U.S. Cl.
CPC ............. *G06V 40/50* (2022.01); *G06F 21/32* (2013.01); *G06V 40/1371* (2022.01); *G06V 40/63* (2022.01); *G06F 2221/2117* (2013.01)

(58) Field of Classification Search
CPC .... G06V 40/50; G06V 40/1371; G06V 40/63; G06V 10/993; G06V 40/12; G06F 21/32; G06F 2221/2117; A61B 5/1172
See application file for complete search history.

(56) References Cited

U.S. PATENT DOCUMENTS

| | | |
|---|---|---|
| 9,361,507 B1 | 6/2016 | Hoyos et al. |
| 2001/0026632 A1 | 10/2001 | Tamai |

(Continued)

FOREIGN PATENT DOCUMENTS

| | | |
|---|---|---|
| JP | 58-031478 | 2/1983 |
| JP | 2001-273498 | 10/2001 |

(Continued)

OTHER PUBLICATIONS

"Full Explanation of the PMC Fingerprint Authentication Mouse", Tronware, vol. 14, No. 2, Apr. 10, 2003, pp. 64-67, along with an English translation thereof.

(Continued)

*Primary Examiner* — Abhishek Sarma
(74) *Attorney, Agent, or Firm* — GREENBLUM & BERNSTEIN, P.L.C.

(57) ABSTRACT

This fingerprint registration method by a user terminal device includes: capturing an image of a fingertip by a camera provided to the user terminal device; generating and displaying an enlarged image obtained by enlarging a fingertip image that includes the captured fingertip; receiving a user operation whether or not the fingertip image is to be registered for fingerprint authentication on the basis of the enlarged image; and transmitting, to an external server as fingerprint data, the fingertip image on which registration operation has been performed through the user operation.

16 Claims, 8 Drawing Sheets

(51) Int. Cl.
*G06V 40/12* (2022.01)
*G06V 40/60* (2022.01)

(56) References Cited

U.S. PATENT DOCUMENTS

| | | |
|---|---|---|
| 2003/0133143 A1 | 7/2003 | McClurg et al. |
| 2003/0142856 A1 | 7/2003 | McClurg et al. |
| 2005/0180619 A1* | 8/2005 | McClurg ............... G06V 40/67 382/124 |
| 2007/0253605 A1* | 11/2007 | Maurer ................. G06T 7/149 382/124 |
| 2010/0303311 A1 | 12/2010 | Shin et al. |
| 2016/0232401 A1 | 8/2016 | Hoyos et al. |
| 2016/0239701 A1 | 8/2016 | Lee et al. |
| 2016/0321496 A1 | 11/2016 | Mather et al. |
| 2018/0018501 A1 | 1/2018 | Mather et al. |
| 2018/0165508 A1* | 6/2018 | Othman .................. G06F 21/32 |
| 2019/0278896 A1 | 9/2019 | Ichikawa et al. |
| 2019/0362130 A1 | 11/2019 | Othman et al. |
| 2020/0110921 A1 | 4/2020 | Mather et al. |

FOREIGN PATENT DOCUMENTS

| | | |
|---|---|---|
| JP | 2004-054835 | 2/2004 |
| JP | 2005-516290 | 6/2005 |
| JP | 2005-352623 | 12/2005 |
| JP | 2013-164717 | 8/2013 |
| JP | 2018-508888 | 3/2018 |
| JP | 2019-074938 | 5/2019 |
| WO | 2018/079001 | 5/2018 |

OTHER PUBLICATIONS

International Search Report issued in International Patent Application No. PCT/JP2020/046315, dated Feb. 2, 2021, along with an English translation thereof.

Japan Office Action issued in Japan Patent Application No. 2021-564065, dated Apr. 4, 2023, together with English translation thereof.

Japan Office Action issued in Japan Patent Application No. 2021-564065, dated Jun. 20, 2023, together with English translation thereof.

Extended European Search Report issued in European Patent Application No. 20899543.1, dated Jan. 2, 2023.

* cited by examiner

FINGERPRINT REGISTRATION METHOD AND USER TERMINAL DEVICE

TECHNICAL FIELD

The present disclosure relates to a fingerprint registration method and a user terminal device.

BACKGROUND ART

Patent Literature 1 discloses a personal authentication device that performs personal authentication based on biometric. The personal authentication device acquires a biometric image by imaging a body part in a non-contact manner, displays the acquired biometric image, and displays a guide image, which indicates an outer shape of the part, so as to be superimposed on the biometric image at an appropriate imaging position. In addition, when it is determined that the body part is imaged at the appropriate imaging position, the personal authentication device extracts biometric information based on the biometric image, matches the biometric information with biometric information registered in advance, and performs the personal authentication.

CITATION LIST

Patent Literature

Patent Literature 1: JP-A-2001-273498

SUMMARY OF INVENTION

Technical Problem

However, in the configuration of Patent Literature 1, since a size of a part (for example, a finger) to be imaged varies depending on users, there is a possibility that an imaging position (that is, a distance suitable for imaging) in a case where a part of a user is imaged in accordance with an outer shape of the displayed guide image deviates from appropriate imaging positions for parts set for the personal authentication device. Accordingly, there is a possibility that a part is not in focus in a biometric image captured by the personal authentication device, and biometric information suitable for fingerprint authentication cannot be extracted.

The present disclosure has been made in view of the above-described circumstances, and an object of the present disclosure is to provide a fingerprint registration method and a user terminal device that support registration of fingerprint data based on a fingertip image captured so as to be suitable for fingerprint authentication.

Solution to Problem

The present disclosure provides a fingerprint registration method to be executed by a user terminal device, including: imaging a fingertip by a camera provided in the user terminal device; generating and displaying an enlarged image in which a fingertip image including the captured fingertip is enlarged; accepting, based on the enlarged image, a user operation as to whether to register the fingertip image for fingerprint authentication; and transmitting, as fingerprint data to an external serve, a fingertip image subjected to a registration operation by the user operation.

In addition, the present disclosure provides a user terminal device communicably connected to an external server, the user terminal device including: a camera that images a fingertip; a processor that generates an enlarged image in which a fingertip image including the fingertip captured by the camera is enlarged; a monitor that displays the generated enlarged image; an operation unit that accepts a user operation as to whether to register the fingertip image for fingerprint authentication; and a communication unit that transmits, as fingerprint data to the external server, the fingertip image registered by the user operation.

Advantageous Effects of Invention

According to the present disclosure, it is possible to support registration of fingerprint data based on a fingertip image captured so as to be suitable for fingerprint authentication.

DESCRIPTION OF EMBODIMENTS (Background of Present Disclosure)

In the related art, in a case where a personal authentication device performs fingerprint registration for fingerprint authentication, a user needs to proceed to a facility (for example, a store, an office, or the like), which uses fingerprint authentication, to register his/her fingerprint, and thus usability is low. As a method for solving such a problem, there is a fingerprint registration method for performing fingerprint registration by a terminal device owned by a user. However, when a user's terminal device (hereinafter referred to as a user terminal device) images a fingerprint of a fingertip of the user himself/herself, the user terminal device includes a wide-angle camera. When the user moves his/her fingertip too close to the user terminal device for imaging, the fingerprint is not in focus, and when the user moves his/her fingertip away from the user terminal device, the fingertip displayed on the user terminal device becomes smaller and it becomes difficult to visually confirm whether the fingerprint is in focus. Thus, it is difficult to have the fingerprint of the fingertip in focus for imaging.

Therefore, in each embodiment described below, an example of a fingerprint registration method and a user terminal device, which support registration of fingerprint data based on a fingertip image captured so as to be suitable for fingerprint authentication, will be described.

Hereinafter, embodiments in which configurations and operations of a fingerprint registration method and a user terminal device according to the present disclosure are specifically disclosed will be described in detail with reference to the drawings as appropriate. Unnecessarily detailed description may be omitted. For example, a detailed description of a well-known matter or a repeated description of substantially the same configuration may be omitted. This is to avoid unnecessary redundancy of the following description and to facilitate understanding for those skilled in the art. The accompanying drawings and the following description are provided for those skilled in the art to sufficiently understand the present disclosure, and are not intended to limit the subject matter described in the claims.

First Embodiment

Figure 1:
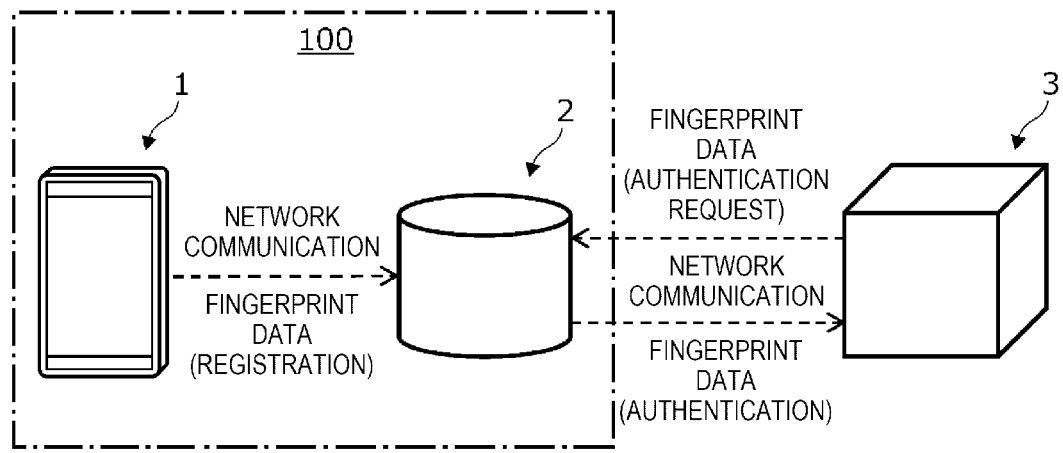
FIG. 1 is an illustrative diagram of a use case example of a fingerprint authentication system according to a first embodiment.
Figure 2:
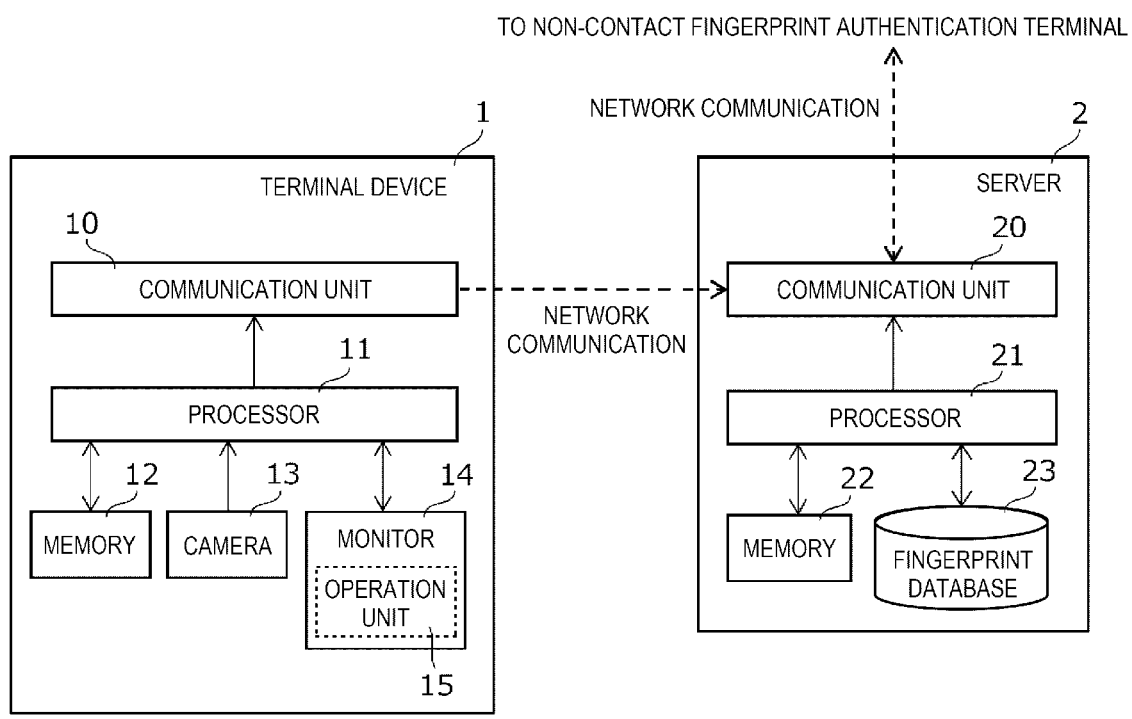
FIG. 2 is a diagram illustrating an example of internal configurations of a user terminal device and a server according to the first embodiment.

A use case and an internal configuration of a fingerprint registration system 100 according to a first embodiment will be described with reference to FIGS. 1 and 2. FIG. 1 is an illustrative diagram of a use case example of the fingerprint registration system 100 according to the first embodiment. FIG. 2 is a diagram illustrating an example of internal configurations of a user terminal device 1 and a server 2 according to the first embodiment. The fingerprint registration system 100 according to the first embodiment includes the user terminal device 1 and the server 2. Further, a non-contact fingerprint authentication device 3 is a device that performs fingerprint authentication by using a fingerprint that is subjected to fingerprint registration performed by the user terminal device 1 and the server 2. In the fingerprint registration system 100 according to the first embodiment, the user terminal device 1 and the server 2 are communicably connected via a network, and transmit and receive data therebetween. Similarly, the server 2 and the non-contact fingerprint authentication device 3 are communicably connected via a network, and transmit and receive data therebetween.

In the fingerprint registration system 100 according to the first embodiment, the fingerprint registration is executed by the user terminal device 1 and the server 2. The fingerprint authentication is executed by the server 2 and the non-contact fingerprint authentication device 3. Although the non-contact fingerprint authentication device 3 illustrated in FIG. 1 is preferably a fingerprint authentication device capable of implementing fingerprint authentication in a hygienic non-contact manner from the viewpoint of being used by a large number of unspecified users, the present invention is not limited thereto.

In the fingerprint registration system 100 according to the first embodiment, the user terminal device 1 images an entire hand or at least one finger of a user based on a user operation, generates fingerprint data for use in fingerprint registration based on a fingerprint of a fingertip reflected in the captured image, and transmits the fingerprint data to the server 2. The user terminal device 1 is implemented by, for example, a smart phone, a tablet terminal, or the like. The user terminal device 1 includes a communication unit 10, a processor 11, a memory 12, a camera 13, a monitor 14, and an operation unit 15. Here, the fingerprint data is data indicating a feature of a fingerprint.

The communication unit 10 is connected to a communication unit 20 in the server 2 via a network so as to be capable of data communication therebetween. The communication unit 10 may be connected to the communication unit 20 in the server 2 so as to be capable of wireless or wired communication. The wireless communication referred to herein is, for example, short-range wireless communication such as Bluetooth® or NFC®, or communication using a wireless local area network (LAN) such as Wifi®. The communication unit 10 transmits the fingerprint data of the user generated by the processor 11, information on the user, and the like to the communication unit 20 in the server 2.

The processor 11 is configured using, for example, a central processing unit (CPU) or a field programmable gate array (FPGA), and performs various types of processing and control in cooperation with the memory 12. Specifically, the processor 11 refers to a program and data held in the memory 12, and executes the program to implement a function related to fingerprint registration (a function of generating fingerprint data based on a fingerprint reflected in a captured image and transmitting the fingerprint data to the server 2), a function of generating a fingertip image based on a captured image, and the like.

When an application capable of executing fingerprint registration is activated by a user operation, the processor 11 generates and outputs a control instruction for causing the camera 13 to start imaging. The processor 11 is input a captured image captured by the camera 13. The processor 11 cuts out a fingertip image including an area of a fingertip, which covers at least from the fingertip to a first joint, from the captured image obtained by imaging an entire hand or at least one finger of the user, the fingertip being of any finger. Here, the fingertip image to be cut out may show a finger that is imaged from at least the fingertip to the first joint and that is most sufficient in focus, or may show a finger that is designated in advance (for example, a middle finger that is easy to image and has the largest area, a finger that is designated by an office, a store or the like that uses the non-contact fingerprint authentication device 3, or the like).

In a case where the entire hand or at least one finger of the user is not present in the captured image captured by the camera 13, the processor 11 generates a notification that no fingertip is reflected.

The processor 11 executes enlargement processing of enlarging the input fingertip image in accordance with a display area set on the monitor 14 of the user terminal device 1, and calculates an evaluation value indicating whether the fingerprint reflected in the input fingertip image is in focus. The evaluation value may be calculated using various known methods, and is calculated by converting into numerical values such as 1 to 100, 1 to 10, or the like. Although the evaluation value in the fingerprint registration system 100 according to the first embodiment will be described assuming that a state of being in focus is set as 100 and a state of not being in focus is set as 1, it is needless to say that the evaluation value is not limited thereto. The processor 11 outputs the fingertip image subjected to the enlargement processing and the calculated evaluation value to the monitor 14 and causes the monitor 14 to display the fingertip image and the calculated evaluation value. When the calculated evaluation value is not equal to or greater than a preset threshold, the processor 11 repeatedly performs the enlargement processing of the captured fingertip image, calculation processing of the evaluation value, and the output thereof.

When the calculated evaluation value is equal to or greater than the threshold, the processor 11 outputs the fingertip image subjected to the enlargement processing and the calculated evaluation value of the fingertip image to the monitor 14, generates a control instruction to display a registration button (see FIGS. 5, 7, and 9) for allowing the user to select whether to execute the fingerprint registration by using the fingertip image, and outputs the control instruction to the monitor 14. The threshold is a value that is set for allowing the fingerprint data to be described later to be generated.

Based on a user operation on the registration button displayed on the monitor 14, the processor 11 generates fingerprint data for the fingerprint registration by using the fingertip image. The fingerprint data referred to herein is data indicating a feature of a fingerprint extracted using a known technique (for example, a minutiae method, a frequency feature analysis method, or the like). Here, the minutiae method is a method of extracting a feature of a fingerprint by detecting an end point indicating a break of a fingerprint line or a branch point (a branching point) among ridges of a fingerprint. In addition, the frequency feature analysis method is a method of extracting a feature of a fingerprint from a waveform of a frequency obtained by converting an unevenness of the fingerprint as the frequency.

The processor 11 transmits the extracted fingerprint data to the server 2, and deletes the fingerprint image used for generating the fingerprint data. In the fingerprint registration system 100 according to the first embodiment, since data used for fingerprint registration is transmitted to the server 2 via a network, privacy of a user may be infringed due to leakage of a fingertip (fingerprint) image when the fingertip image is transmitted to the server 2. Since the user terminal device 1 transmits fingerprint data as the data used for fingerprint registration that is generated by extracting a feature of a fingerprint, it is possible to extremely reduce the possibility of infringement on the privacy of the user even when the fingerprint data is leaked. Therefore, regarding the data used for fingerprint registration in the fingerprint registration system 100 according to the first embodiment, it is preferable to use the fingerprint data, which is generated by extracting the feature of the fingerprint reflected in the fingertip image, to execute the fingerprint registration for the purpose of security improvement, but the present invention is not limited thereto. For example, the user terminal device 1 may transmit data of the fingertip image, for which an evaluation value equal to or greater than the preset threshold is calculated, and execute the fingerprint registration. In such a case, the server 2 detects the fingertip (fingerprint) of the user based on the data of the fingertip image transmitted from the user terminal device 1, extracts the feature of the detected fingerprint to generate fingerprint data, and performs fingerprint registration using the generated fingerprint data. The data used for the fingerprint registration is preferably encrypted and transmitted.

In the fingerprint registration system 100 according to the first embodiment, the fingerprint data may be generated so as to be able to be authenticated by a plurality of known techniques. For example, the fingerprint data may be a plurality of types of fingerprint data generated by the minutiae method and the frequency feature analysis method, respectively. Accordingly, even when the non-contact fingerprint authentication device 3 executes fingerprint authentication using fingerprint data generated by a different method rather than using a fingertip (fingerprint) image, the fingerprint registration system 100 can execute the fingerprint authentication using the corresponding fingerprint data. Accordingly, the fingerprint registration system 100 according to the first embodiment can execute fingerprint authentication without using a fingertip (fingerprint) image, can prevent leakage of a fingertip (fingerprint) image transmitted from the non-contact fingerprint authentication device 3 to the server 2 via the network, and can improve security.

The memory 12 includes, for example, a random access memory (RAM) as a work memory to be used when executing various types of processing of the processor 11, and a read only memory (ROM) that stores a program and data defining an operation of the processor 11. The RAM temporarily stores data or information generated or acquired by the processor 11. A program that defines an operation of the processor 11 is written in the ROM. The memory 12 stores a threshold related to an evaluation value of a fingertip image, a display area of the monitor 14, and user-related information (for example, personal information possible for identifying an individual user, an employee number, card information used for payment) transmitted to the server 2 and stored in association with fingerprint data, and the like. The user-related information may be input by a user at the time of transmission of fingerprint data, and may be deleted when the transmission of the fingerprint data is completed.

The camera 13 includes at least a lens (not shown) and an image sensor (not shown). The image sensor is, for example, a solid-state imaging device such as a charge-coupled device (CCD) or a complementary metal oxide semiconductor (CMOS), and converts an optical image formed on an imaging surface into an electric signal. The camera 13 starts imaging by an imaging start control instruction input by the processor 11 or an imaging operation of the user. The camera 13 outputs the captured image to the processor 11.

The monitor 14 is configured using, for example, a liquid crystal display (LCD) or an organic electroluminescence (EL). The monitor 14 displays a captured image captured by the camera 13, a fingertip image subjected to the enlargement processing of the processor 11, an evaluation value, a registration button (see FIGS. 5, 7, and 9), and the like. In addition, when an alert is input from the processor 11 to a user for instructing imaging of a fingertip, the monitor 14 displays the alert, or outputs the alert by voice with a speaker (not shown).

The monitor 14 may be a touch interface provided in the user terminal device 1 and implemented by a touch panel. In such a case, the monitor 14 has a function as the operation unit 15, accepts an input operation of the user, and outputs a result of the input operation of the user to the processor 11.

The operation unit 15 can accept a user operation such as a startup operation of an application, an imaging operation of the camera 13, a selection (registration) operation of a finger or a fingertip image used for fingerprint registration, and an input operation of user-related information, and outputs a result of the input operation to the processor 11. The operation unit 15 may be implemented as a touch panel of the monitor 14 described above. The operation unit 15 may include a microphone (not shown), and may accept a voice input operation based on a voice of the user.

The server 2 as an example of an external server in the fingerprint registration system 100 according to the first embodiment stores fingerprint data and user-related information, which are received from the user terminal device 1, in association with each other (that is, performs fingerprint registration), and matches each of a plurality of pieces of stored fingerprint data with fingerprint data or fingertip (fingerprint) image received from the non-contact fingerprint authentication device 3 to determine whether the received fingerprint data can be authenticated (that is, performs fingerprint authentication). The server 2 includes the communication unit 20, a processor 21, a memory 22, and a fingerprint database 23.

The communication unit 20 is communicably connected to the communication unit 10 in the user terminal device 1 and the non-contact fingerprint authentication device 3 via a network, and is capable of data communication therebetween. The communication unit 20 may be connected to the communication unit 10 in the user terminal device 1 so as to be capable of wireless communication. The wireless communication referred to herein is, for example, short-range wireless communication such as Bluetooth® or NFC®, or communication using a wireless local area network (LAN) such as Wifi®. The communication unit 20 receives fingerprint data and user-related information from the communication unit 10 in the user terminal device 1. Further, the communication unit 20 receives fingerprint data to be matched from the non-contact fingerprint authentication device 3, and transmits information on whether the received fingerprint data can be authenticated.

The processor 21 is configured using, for example, a central processing unit (CPU) or a field programmable gate array (FPGA), and performs various types of processing and control in cooperation with the memory 22. Specifically, the processor 21 refers to a program and data held in the memory 22, and executes the program to implement a function of storing fingerprint data and user-related information, which are received from the user terminal device 1, in association with each other as a function related to fingerprint registration, and a function of determining whether fingerprint data received from the non-contact fingerprint authentication device 3 can be authenticated as a function related to fingerprint authentication.

The processor 21 associates the fingerprint data with the user-related information that are received from the user terminal device 1, outputs the fingerprint data to the fingerprint database 23, and stores the fingerprint data in the fingerprint database 23.

When fingerprint data is received from the non-contact fingerprint authentication device 3, the processor 21 refers to the fingerprint database 23 and determines whether there is fingerprint data, among a plurality of pieces of stored fingerprint data, matching the received fingerprint data. When there is matching fingerprint data as a result of the determination, the processor 21 generates a notification indicating that the authentication is possible, and transmits the notification to the non-contact fingerprint authentication device 3 via the communication unit 20. On the other hand, when there is no matching fingerprint data as a result of the determination, the processor 21 generates a notification indicating that the authentication is not possible, and transmits the notification to the non-contact fingerprint authentication device 3 via the communication unit 20.

The memory 22 includes, for example, a random access memory (RAM) as a work memory to be used when executing various types of processing of the processor 21, and a read only memory (ROM) that stores a program and data defining an operation of the processor 21. The RAM temporarily stores data or information generated or acquired by the processor 21. A program that defines an operation of the processor 21 is written in the ROM.

The fingerprint database 23 is what is called a storage, and stores fingerprint data input from the processor 21 for each user as user-related information and fingerprint data. The fingerprint database 23 may be an external storage that is externally connected to the server 2 and is provided separately from the server 2.

The non-contact fingerprint authentication device 3 is installed in, for example, a facility (an office, a store, or the like) that performs fingerprint authentication, transmits a fingertip (fingerprint) image or fingerprint data of a user acquired in a non-contact state to the server 2, and performs fingerprint authentication by matching. Although an example is describe in which the non-contact fingerprint authentication device 3 illustrated in FIG. 1 can acquire a fingertip (fingerprint) image or fingerprint data of a user in a non-contact state, the present invention is not limited thereto as long as the fingerprint authentication can be executed. The non-contact fingerprint authentication device 3 illustrated in FIG. 1 includes a communication unit for enabling the above-described functions to be executed, a processor, a memory, a camera capable of imaging a fingerprint, a fingerprint sensor, and the like, but illustration and description thereof are omitted.

Figure 3:
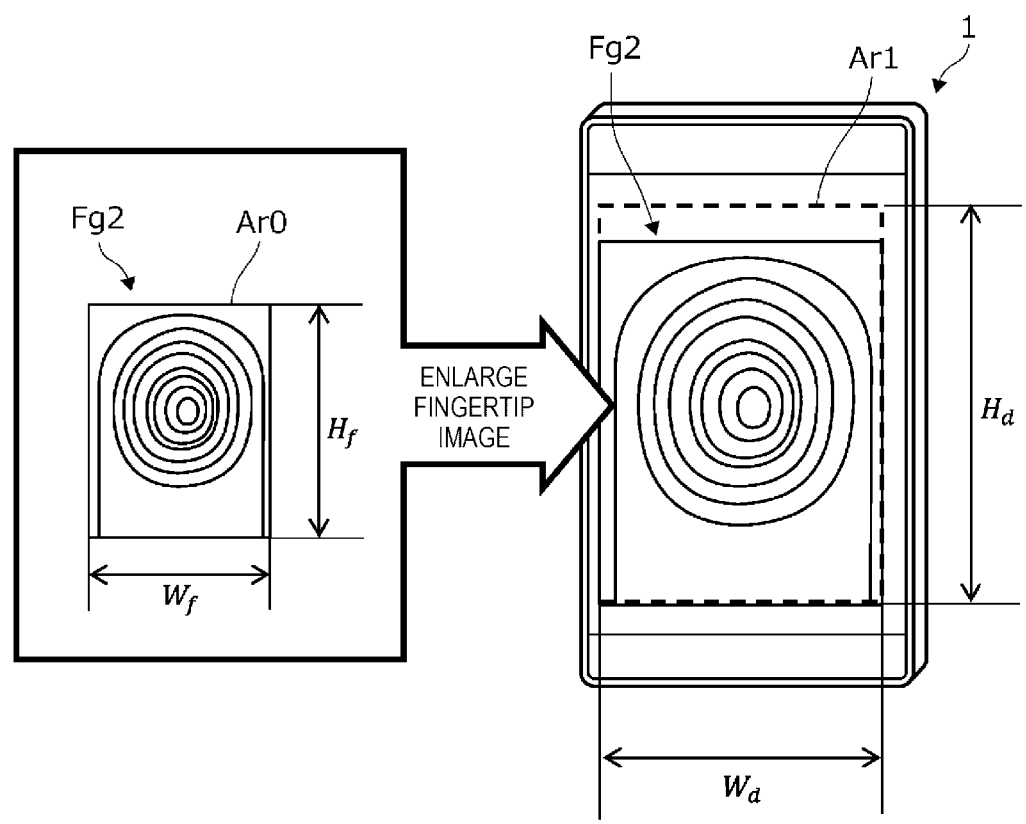
FIG. 3 is a diagram illustrating an enlargement and display example of a fingertip image.

Next, enlargement processing of a fingertip image Fg2 executed in the user terminal device 1 will be described with reference to FIG. 3. FIG. 3 is a diagram illustrating an enlargement and display example of the fingertip image Fg2. FIG. 3 illustrates an example in which the processor 11 enlarges the fingertip image Fg2, which is cut out including at least a first joint, in accordance with a display area Ar1 of the user terminal device 1.

The fingertip image Fg2 illustrated in FIG. 3 is cut out by the processor 11 at a cutout area Ar0 (with a longitudinal width Hf and a transverse width Wf). On the monitor 14 of the user terminal device 1 illustrated in FIG. 3, the display area Ar1 (with a longitudinal width Hd and a transverse width Wd) in which the enlarged fingertip image Fg2 is displayed is set. The display area Ar1 referred to herein is a predetermined area set in advance with respect to an entire area of the monitor 14 in the user terminal device 1, and is an area for enlarging and displaying the fingertip image Fg2.

The processor 11 executes the enlargement processing while maintaining an aspect ratio of the fingertip image Fg2 so that the longitudinal width of the fingertip image Fg2 corresponds to the longitudinal width of the display area Ar1 or the transverse width of the fingertip image Fg2 corresponds to the transverse width of the display area Ar1. Here, a method of calculating an enlargement magnification $\alpha 1$ in the enlargement processing of the fingertip image Fg2 will be described.

First, the processor 11 calculates a magnification $\alpha H$ in a longitudinal direction and a magnification $\alpha W$ in a transverse direction of the fingertip image Fg2. The magnification $\alpha H$ in the longitudinal direction is calculated using (the longitudinal width Hd of the display area Ar1)/(the longitudinal width Hf of the fingertip image Fg2). The magnification $\alpha W$ in the transverse direction is calculated using (the transverse width Wd of the display area Ar1)/(the transverse width Wf of the fingertip image Fg2). Next, the processor 11 compares the calculated magnification $\alpha H$ in the longitudinal direction with the calculated magnification $\alpha W$ in the transverse direction, uses the smaller magnification as the enlargement magnification $\alpha 1$ of the fingertip image Fg2, and executes the enlargement processing of the fingertip image Fg2. In a case where the two magnifications are of the same value, the magnification $\alpha H$ in the longitudinal direction may be adopted, or the magnification $\alpha W$ in the transverse direction may be adopted.

Accordingly, the fingerprint registration system 100 according to the first embodiment can perform enlargement processing on the fingertip image Fg2 of a user correspondingly to the display area Ar1 of the user terminal device 1, and facilitates visual confirmation of whether the fingertip image Fg2 captured by the user is in focus. Therefore, in fingerprint registration using a fingertip image Fg2 (fingerprint image) captured by the user terminal device 1, the fingerprint registration system 100 according to the first embodiment can support imaging to obtain a fingertip image Fg2 (fingerprint image) suitable for fingerprint authentication. Further, the user can adjust an imaging angle and an imaging distance for a fingertip to be imaged by the user terminal device 1 while visually confirming the fingertip image Fg2 displayed in an enlarged manner in the display area Ar1, and can easily perform imaging to obtain a fingertip (fingerprint) image.

Although the example in which the enlarged fingertip image Fg2 is displayed in the display area Ar1 of the fingertip image of the monitor 14 is described above, the example of enlargement display processing of the fingertip image Fg2 is not limited thereto. Next, an example in which the display area is further limited with respect to the display area Ar1 (in other words, an example of enlargement/ reduction display processing of the fingertip image Fg2 displayed in the display area Ar1) will be described.

When the display area is further limited with respect to the display area Ar1, the processor 11 multiplies the enlargement magnification α1 by an enlargement/reduction magnification β (0<β≤1) set in advance to enlarge/reduce the display area. Accordingly, the fingertip image Fg2 is displayed on the monitor 14 in a size corresponding to the display area enlarged/reduced by the enlargement/reduction magnification β. The enlargement/reduction magnification β may be set by a user operation.

Here, in the example illustrated in FIG. 3, an example is shown in which relationships between the longitudinal width and the transverse width of the cutout area Ar0 and those of the display area Ar1 are the longitudinal width Hd>the longitudinal width Hf and the transverse width Wd>the transverse width Wf, but it is needless to say that the relationships are not limited thereto. When the relationships between the longitudinal width and the transverse width of the cutout area Ar0 and those of the display area Ar1 are the longitudinal width Hd<the longitudinal width Hf and the transverse width Wd<the transverse width Wf, the processor 11 may execute reduction processing.

In the execution of the reduction processing, first, the processor 11 calculates the magnification αH in the longitudinal direction using (the longitudinal width Hd of the display area Ar1)/(the longitudinal width Hf of the fingertip image Fg2), and calculates the magnification αW in the transverse direction using (the transverse width Wd of the display area Ar1)/(the transverse width Wf of the fingertip image Fg2). Next, the processor 11 compares the calculated magnification αH in the longitudinal direction with the calculated magnification αW in the transverse direction, uses the smaller magnification as a reduction magnification α2 of the fingertip image Fg2, and executes the reduction processing of the fingertip image Fg2.

Figure 4:
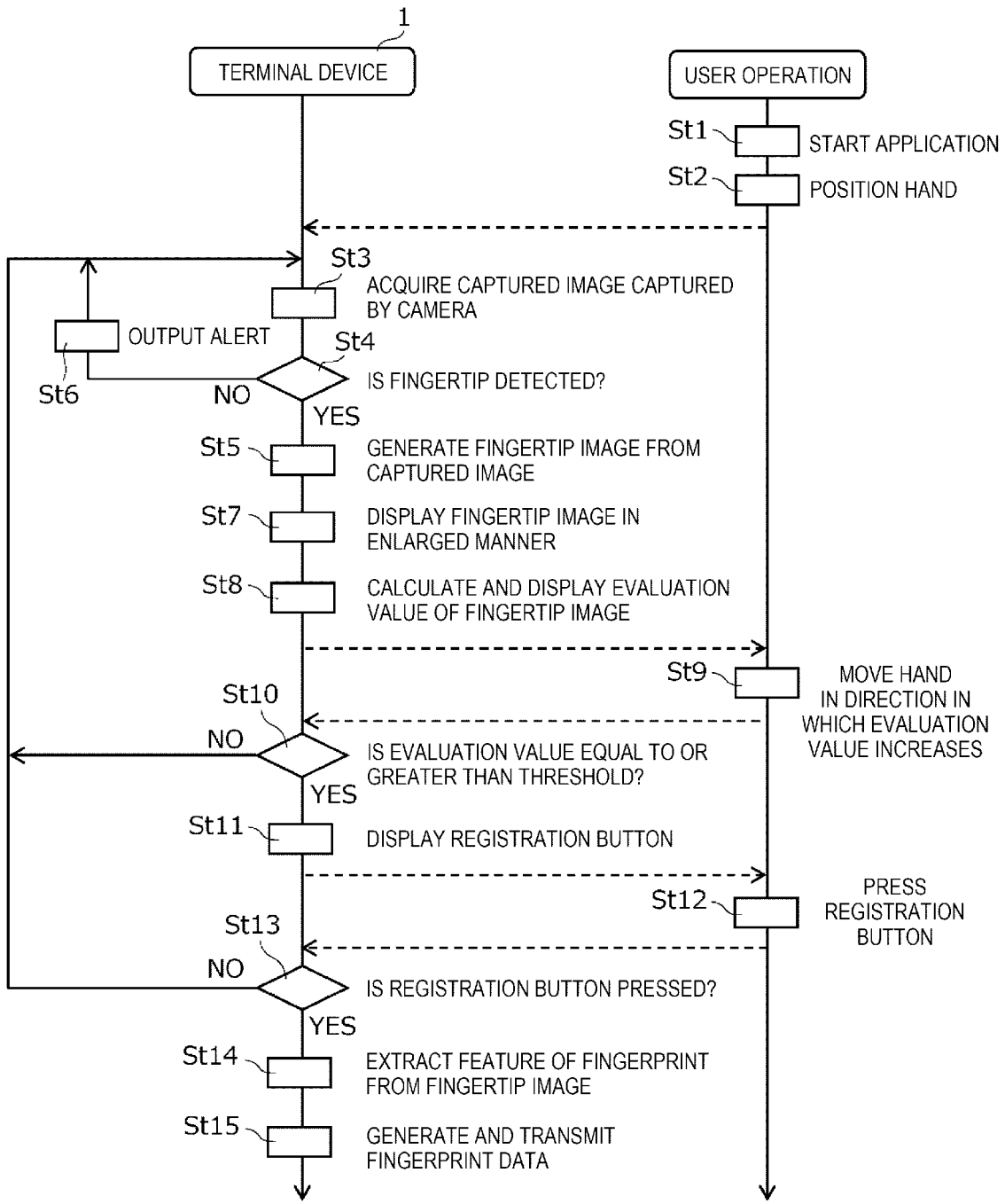
FIG. 4 is a sequence diagram illustrating an operation procedure and action procedure example of the user terminal device according to the first embodiment.
Figure 5:
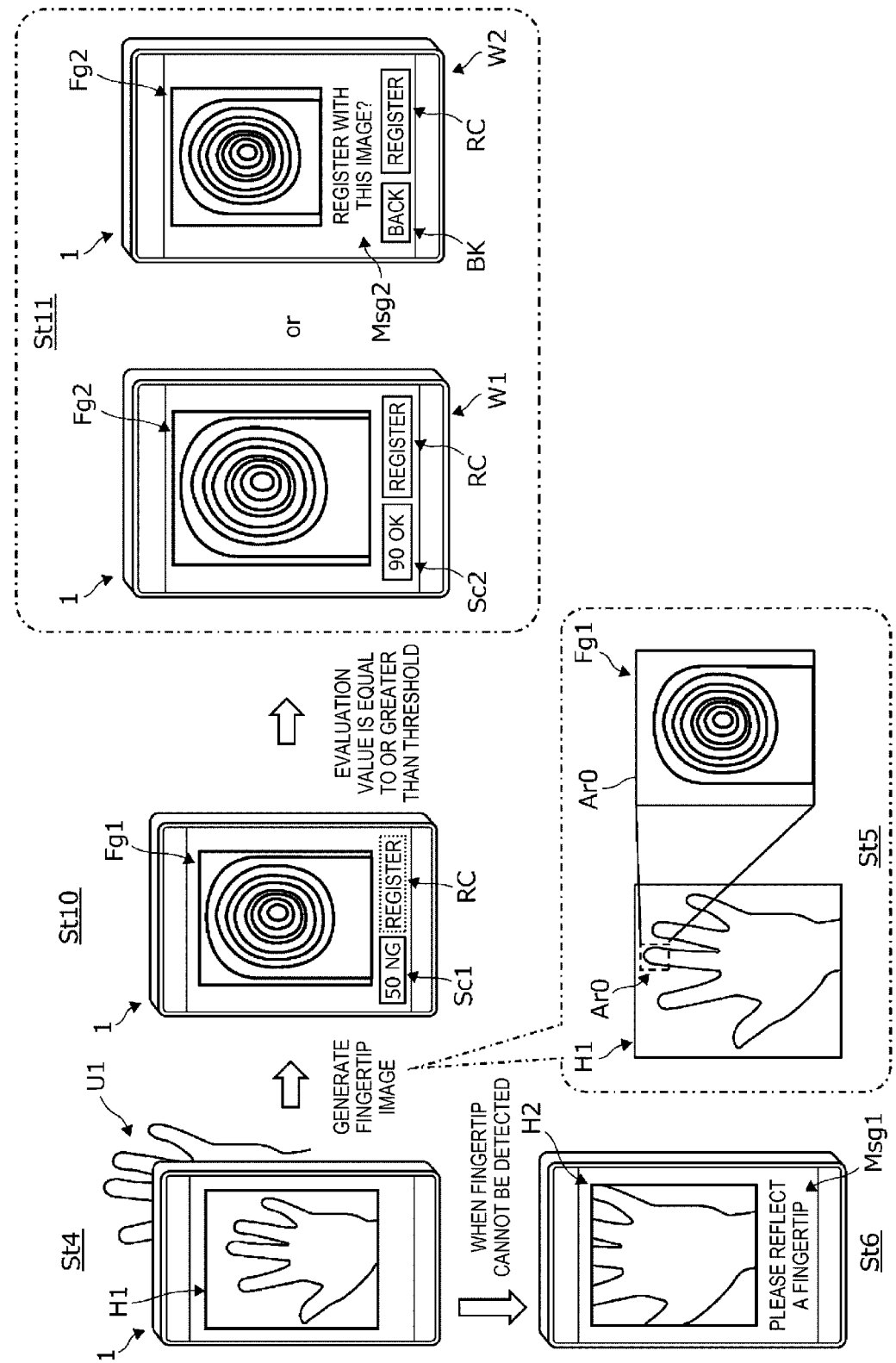
FIG. 5 is a diagram illustrating the operation procedure and action procedure example of the user terminal device according to the first embodiment.

An operation procedure and action procedure example of the user terminal device 1 according to the first embodiment will be described with reference to FIGS. 4 and 5. FIG. 4 is a sequence diagram illustrating the operation procedure and action procedure example of the user terminal device 1 according to the first embodiment. FIG. 5 is a diagram illustrating the operation procedure and action procedure example of the user terminal device 1 according to the first embodiment. In the example illustrated in FIG. 5, an evaluation value 80 of evaluation values 1 to 100 is set as a threshold.

First, a user operates the user terminal device 1 to start an application capable of executing fingerprint registration (St1). The user terminal device 1 starts the application based on a user operation, and generates and outputs a control instruction to start imaging to the camera 13. The user positions his/her entire hand or one finger including at least a first joint, in an imaging area of the camera 13 provided in the user terminal device 1 (St2).

The camera 13 outputs a captured image H1 to the processor 11. The processor 11 acquires the captured image H1 captured by the camera 13 (St3), and displays the captured image H1 on the monitor 14. Further, the processor 11 performs image analysis on the captured image H1, and detects a fingertip including at least a first joint (St4). In step St4 illustrated in FIG. 5, the user terminal device 1 displays the captured image H1 obtained by imaging a hand U1 of the user, and performs detection of a fingertip including at least a first joint.

When a fingertip including at least a first joint is detected from the captured image H1 in the processing of step St4 (St4, YES), the processor 11 determines and cuts out the cutout area Ar0 including at least the first joint, and generates the fingertip image Fg1 (St5).

On the other hand, when no fingertip including at least a first joint is detected as in a captured image H2 illustrated in FIG. 5 in the processing of step St4 (St4, NO), the processor 11 generates an alert Msg1 "Please reflect a fingertip" as a notification reporting that no fingertip is detected, and outputs the alert Msg1 to the monitor 14 and displays the alert Msg1 on the monitor 14 (St6). The alert Msg1 may be output by voice. After the processing of step St6, the processor 11 proceeds to the processing of step St3, and acquires a captured image from the camera 13 again.

The processor 11 calculates the enlargement magnification α1 based on the longitudinal width Hd and the transverse width Wd of the display area Ar1 stored in the memory 12 and the longitudinal width Hf and the transverse width Wf of the cutout area Ar0 of the fingertip image Fg1, and executes enlargement processing on the fingertip image Fg1. The processor 11 outputs the enlarged fingertip image Fg1 to the monitor 14 and displays the fingertip image Fg1 on the monitor 14 (St7).

Further, the processor 11 calculates an evaluation value indicating whether a fingerprint reflected in the fingertip image Fg1 is in focus, and outputs the calculated evaluation value to the monitor 14 to be displayed thereon (St8). The evaluation value displayed here may be displayed including a result of processing executed in step St10 described later (that is, determination processing of whether the calculated evaluation value is equal to or greater than the set threshold), such as "50 NG" of an evaluation result Sc1 and "90 OK" of an evaluation result Sc2 illustrated in FIG. 5. Accordingly, the user can visually confirm whether the fingerprint reflected in the fingertip image Fg1 is in focus according to the fingertip image Fg2 and the evaluation results Sc1 and Sc2.

The user moves his/her hand in a direction in which the evaluation value increases while visually confirming the fingertip image and the evaluation value displayed on the monitor 14 (St9).

In the example illustrated in FIG. 5, the evaluation value 80 is set as the threshold. When the evaluation value is calculated to be 90 as in the example illustrated in step St11 illustrated in FIG. 5 and is equal to or greater than the set threshold in the processing of step St10 (that is, a state where the imaged fingerprint is in sufficient focus) (St10, YES), as illustrated in a registration screen W1 and a registration screen W2, acceptance of an input operation of the user on the monitor 14 is possible, and the processor 11 enables an input operation of a registration button RC for executing the fingerprint registration using the fingertip image Fg2 for which the evaluation value equal to or greater than the threshold is calculated (St11). The processor 11 may display a return button BK (see FIG. 5) by which an input operation in a case where the fingerprint registration using the fingertip image Fg2 is not to be executed can be accepted. Further, the processor 11 may cause the user to visually confirm the fingertip image Fg2, generate a message Msg2 to ask the user whether to execute the fingerprint registration using the fingertip image Fg2, and display the message Msg2 on the monitor 14. Note that the processor 11 may generate a message or notification (for example, "The fingerprint is clearly reflected?") for requesting the visual confirmation of the fingertip image Fg2 (that is, the enlarged image), and display the message or notification on the monitor 10 together with the message Msg2 illustrated in FIG. 5.

On the other hand, when the evaluation value of the fingertip image Fg1 is calculated to be 50 as in the example illustrated in step St10 illustrated in FIG. 5 and is less than the set threshold in the processing of step St10 (that is, a state where the imaged fingerprint is not in sufficient focus) (St10, NO), the processor 11 proceeds to the processing of step St3, and acquires a captured image from the camera 13 again. In such a case, as illustrated in FIG. 5, the registration button RC may be displayed so as not to accept an input operation of the user.

The user terminal device 1 repeatedly performs the processing of steps St3 to St8 until the calculated evaluation value is determined to be equal to or greater than the threshold in the processing of step St10. Therefore, when the evaluation value is less than the set threshold, the user performs the action illustrated in step St9 while visually confirming the enlarged fingertip image and the evaluation value of the fingertip image that are displayed on the monitor 14. Accordingly, the user can visually confirm whether the fingerprint is in focus in the enlarged fingertip image, and can visually confirm whether the finger is in focus based on a numerical value indicated by the displayed evaluation value.

When the fingerprint registration using the fingertip image Fg2 for which an evaluation value equal to or greater than the threshold is calculated is to be executed, the user presses the registration button RC (St12).

The processor 11 determines whether the registration button RC is pressed by the user (St13). When the registration button RC is pressed (St13, YES), the processor 11 extracts a feature of the fingerprint reflected in the fingertip image Fg2 (St14). On the other hand, when the registration button RC is not pressed (St13, NO), the processor 11 proceeds to the processing of step St3, and acquires a captured image from the camera 13 again. When the return button BK is pressed by the user operation in the processing of step St11, the processor 11 proceeds to the processing of step St3.

The processor 11 converts the extracted fingerprint feature into data, and generates fingerprint data for fingerprint registration. The processor 11 transmits the generated fingerprint data to the server 2 (St15), and deletes the fingertip image Fg2 used for generating the fingerprint data.

As described above, the fingerprint registration system 100 according to the first embodiment can perform the enlargement processing on the fingertip image Fg2 of the user in correspondence with the display area in the user terminal device 1, and facilitates visual confirmation of whether the fingertip image captured by the user is in focus. In addition, in fingerprint registration using fingerprint data that is based on a fingertip (fingerprint) image captured by the user terminal device 1, the fingerprint registration system 100 according to the first embodiment can support imaging to obtain a fingertip (fingerprint) image suitable for fingerprint authentication. Further, when the evaluation value is equal to or less than the threshold, the user can adjust the imaging angle, the imaging distance, and the focus of the fingertip to be imaged by the user terminal device 1 while visually confirming the fingertip image displayed in an enlarged manner in the display area, and can easily perform imaging to obtain the fingertip (fingerprint) image.

As described above, the fingerprint registration system 100 according to the first embodiment is a system capable of implementing a fingerprint registration method using the user terminal device 1. The fingerprint registration system 100 images a fingertip of a person, who performs fingerprint registration, by using the camera 13 provided in the user terminal device 1, generates and displays an enlarged image in which a fingertip image including the imaged fingertip is enlarged, accepts, based on the enlarged image, a user operation as to whether to register the fingertip image for fingerprint authentication, and transmits, as fingerprint data to an external server (that is, the server 2), the fingertip image subjected to a registration operation by the user operation.

Accordingly, since the fingerprint registration system 100 according to the first embodiment enlarges and displays the fingertip image of the user, visual confirmation performed by the user as to whether a fingerprint of the fingertip image is in focus is facilitated. In addition, in fingerprint registration using fingerprint data that is based on a fingertip (fingerprint) image captured by the user terminal device 1, the fingerprint registration system 100 according to the first embodiment can support imaging to obtain a fingertip (fingerprint) image suitable for fingerprint authentication.

The fingerprint data is data that is obtained by extracting, based on a fingertip image, a fingerprint feature for performing fingerprint authentication. Accordingly, since the fingerprint registration system 100 according to the first embodiment uses the fingerprint data extracted from the fingerprint image instead of the fingerprint image itself, the leakage of the fingertip image reflecting a fingerprint can be prevented and the security can be improved.

The fingerprint registration system 100 according to the first embodiment displays, together with the enlarged image, a notification (message) for requesting the user to visually confirm the enlarged image. Accordingly, the fingerprint registration system 100 according to the first embodiment can execute fingerprint registration using fingerprint data that is based on a fingertip (fingerprint) image for which it is visually confirmed by the user whether a fingerprint of the fingertip image is in focus.

Further, the fingerprint registration system 100 according to the first embodiment calculates, based on a fingertip image, an evaluation value indicating whether a fingerprint reflected in the fingertip image is in focus, and displays the calculated evaluation value together with the enlarged image. Accordingly, the fingerprint registration system 100 according to the first embodiment can visualize, by the evaluation value, whether the fingertip image is suitable for the fingerprint authentication, and can support, by displaying the evaluation value and the enlarged image, user determination as to whether the fingertip (fingerprint) image is suitable for fingerprint registration. Therefore, the user can efficiently perform the fingerprint registration with the evaluation value and the enlarged image.

Further, the fingerprint registration system 100 according to the first embodiment calculates, based on a fingertip image, an evaluation value indicating whether a fingerprint reflected in the fingertip image is in focus, and enables acceptance of a registration operation when the evaluation value exceeds a threshold. Accordingly, the fingerprint registration system 100 according to the first embodiment can enable fingerprint registration of only a fingertip (fingerprint) image determined to be captured in a focused state so as to be suitable for fingerprint authentication, and can efficiently support fingerprint registration using fingerprint data that is based on the fingerprint (fingertip) image.

Further, the fingerprint registration system 100 according to the first embodiment calculates, based on a fingertip image, an evaluation value indicating whether a fingerprint reflected in the fingertip image is in focus. When the evaluation value does not exceed a threshold, the fingerprint registration system 100 regenerates a fingertip image and recalculates an evaluation value corresponding to the regenerated fingertip image, and repeats the regeneration of a fingertip image and the recalculation of an evaluation value based on the regenerated fingertip image until a recalculated evaluation value exceeds the threshold. Accordingly, the fingerprint registration system 100 according to the first embodiment repeats the imaging and the calculation of an evaluation value until it is determined that a fingertip image is captured in a focused state so as to be suitable for fingerprint authentication, and thus it is possible to efficiently support fingerprint registration using fingerprint data that is based on an effective fingerprint (fingertip) image.

In addition, the fingerprint registration system 100 according to the first embodiment images a fingertip based on an imaging operation of a user. Accordingly, the fingerprint registration system 100 according to the first embodiment can generate fingerprint data based on a fingertip image including a fingertip captured based on the imaging operation of the user.

In addition, the fingerprint registration system 100 according to the first embodiment compares an enlargement magnification in a longitudinal direction that is calculated based on a longitudinal width of a fingertip image and a longitudinal width of a display area of a user terminal device on which an enlarged image is displayed, and an enlargement magnification in a transverse direction that is calculated based on a transverse width of the fingertip image and a transverse width of the display area, and enlarges and generates the fingertip image by using the smaller enlargement magnification. Accordingly, the fingerprint registration system 100 according to the first embodiment can enlarge the fingertip image within the display area of the user terminal device 1 while maintaining an aspect ratio of the fingertip image, and can facilitate visual confirmation for the user.

After transmitting the fingerprint data to an external server, the fingerprint registration system 100 according to the first embodiment deletes the fingertip image subjected to the registration operation from the user terminal device 1. Accordingly, the fingerprint registration system 100 according to the first embodiment can prevent the fingertip image stored in the user terminal device 1 from being reused by a user or a person other than the user, and can improve security of the registered fingerprint data.

In addition, when no fingertip of the user is reflected in the imaging area of the camera 13, the fingerprint registration system 100 according to the first embodiment outputs an alert indicating that no fingertip is present in the imaging area. Accordingly, the fingerprint registration system 100 can notify the user that no fingertip is imaged.

As described above, the user terminal device 1 in the fingerprint registration system 100 according to the first embodiment is a user terminal device 1 communicably connected to an external server, and includes the camera 13 that images a fingertip, the processor 11 that generates an enlarged image in which a fingertip image including a fingertip captured by the camera 13 is enlarged, the monitor 14 that displays the generated enlarged image, an operation unit 15 that accepts a user operation as to whether to register the fingertip image for fingerprint authentication, and the communication unit 10 that transmits fingerprint data for performing fingerprint authentication to the external server. In addition, the processor 11 in the user terminal device 1 detects a fingerprint reflected in the fingertip image for which a registration operation of the fingertip image performed by a user is accepted via the operation unit 15, extracts, based on a fingerprint image, a feature of the fingerprint for performing the fingerprint authentication, and generates the fingerprint data.

Accordingly, since the user terminal device 1 in the fingerprint registration system 100 according to the first embodiment enlarges and displays the fingertip image of the user, visual confirmation performed by the user as to whether the fingerprint of the fingertip image is in focus is facilitated. In addition, in fingerprint registration using fingerprint data that is based on a captured fingertip (fingerprint) image, the user terminal device 1 supports imaging to obtain a fingertip (fingerprint) image suitable for fingerprint authentication, and uses fingerprint data extracted from the fingerprint image instead of the fingerprint image itself. Accordingly, the leakage of the fingertip image reflecting a fingerprint can be prevented and the security can be improved. Therefore, the user terminal device 1 can support registration of fingerprint data that is based on a fingertip image captured so as to be suitable for fingerprint authentication, without causing a user to go to a facility that uses fingerprint authentication.

Second Embodiment

The example is illustrated in which the fingerprint registration system 100 according to the first embodiment detects one fingertip including at least a first joint from an entire hand or fingers reflected in a captured image. With respect to the fingerprint registration system 100 according to a second embodiment, an example will be described. In the example, a guide indicating an imaging position of one fingertip, which includes at least a first joint and is for registering a fingerprint thereof, is superimposed and displayed on a captured image displayed on the monitor 14, and a fingertip in an area including a peripheral area of the guide is detected.

Figure 6:
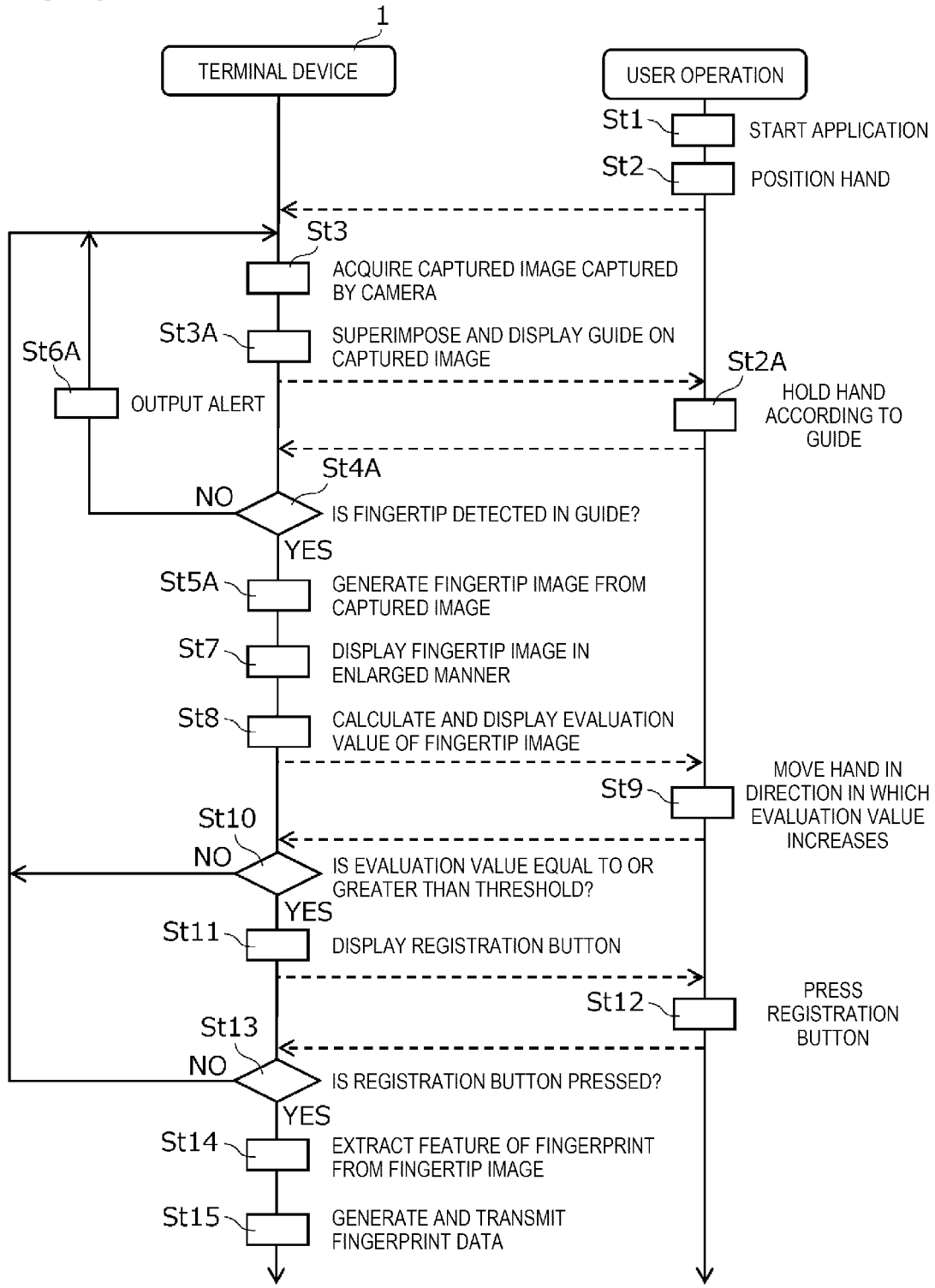
FIG. 6 is a sequence diagram illustrating an operation procedure and action procedure example of a user terminal device according to second embodiment.
Figure 7:
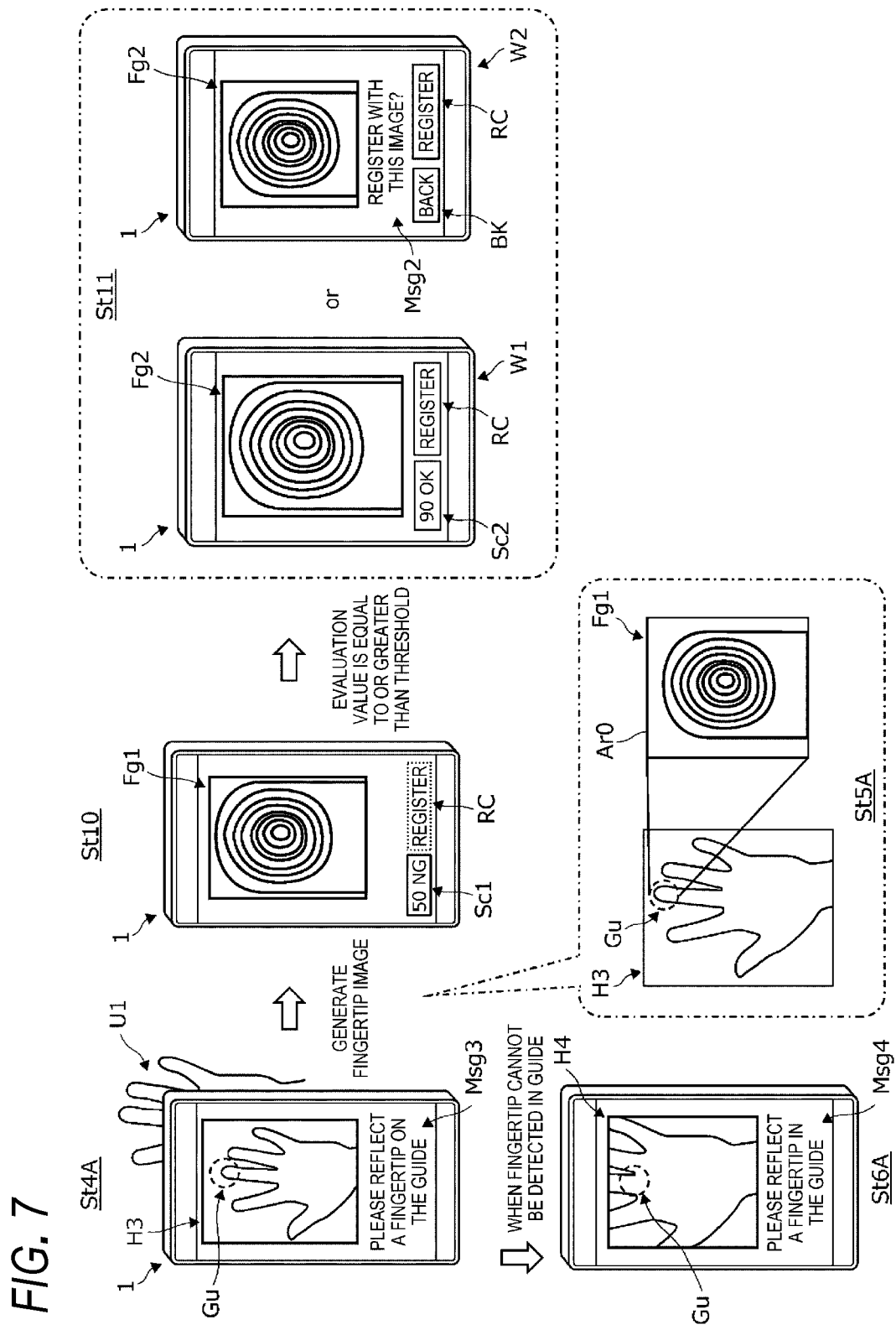
FIG. 7 is a diagram illustrating the operation procedure and action procedure example of the user terminal device according to the second embodiment.

An operation procedure and action procedure example of the user terminal device 1 according to the second embodiment will be described with reference to FIGS. 6 and 7. FIG. 6 is a sequence diagram illustrating the operation procedure and action procedure example of the user terminal device 1 according to the second embodiment. FIG. 7 is a diagram illustrating the operation procedure and action procedure example of the user terminal device 1 according to the second embodiment. In the example illustrated in FIG. 7, an evaluation value 80 of evaluation values 1 to 100 is set as a threshold. In steps St1 to St3 and steps St7 to St15 in the operation procedure and action procedure example of the user terminal device 1 according to the second embodiment, substantially the same processing as that in the operation procedure and action procedure example of the user terminal device 1 according to the first embodiment illustrated in FIG. 4 is executed. Therefore, the same operation procedures or action procedures as those in the first embodiment are denoted by the same reference signs, and a description thereof will be omitted.

The processor 11 superimposes a guide Gu, which indicates an imaging position of one fingertip including at least a first joint, on a captured image H3 that is acquired from the camera 13 in step St3, and outputs the guide Gu to the monitor 14 (St3A). Here, a superimposition position of the guide Gu may be superimposed on a position of any fingertip detected from the captured image H3, or may be superimposed on a position subjected to a selection (setting) operation for a finger to be imaged from the user when the selection (setting) operation is accepted after the start of an application. Although a shape of the guide Gu illustrated in FIG. 7 is circular, the shape of the guide Gu is not limited thereto, and may be, for example, an elliptical shape, a rectangular shape, a square shape, or the like. Further, in the second embodiment, the processor 11 may change a size of an outer shape of the guide Gu based on an angle of view, which is stored in the memory 12, of the camera 13 provided in the user terminal device 1. When there is a selection (setting) operation performed by the user with respect to a finger to be imaged, the processor 11 may change the size of the outer shape of the guide Gu according to the selected (set) finger.

The user positions his/her hand so that the fingertip is positioned at the imaging position indicated by the displayed guide Gu (St2A).

The processor 11 detects whether there is one fingertip including at least a first joint in an area including a peripheral area of the guide Gu (St4A). Note that, as in the example illustrated in step St4A illustrated in FIG. 7, the processor 11 may generate and display a message Msg3 "Please reflect a fingertip on the guide" indicating an instruction to perform imaging so that a fingertip is positioned on the guide Gu. The message Msg3 may be output by voice.

When the processor 11 detects a fingertip including at least a first joint in the guide Gu in the processing of step St4A (St4A, YES), the processor 11 cuts out the cutout area Ar0 including the imaging area indicated by the guide Gu superimposed on the captured image H3, and generates the fingertip image Fg1 (St5A).

On the other hand, when no fingertip including at least a first joint is detected in the guide Gu, as in a captured image H4 illustrated in step St6A illustrated in FIG. 7, in the processing of step St4A (St4A, NO), the processor 11 generates an alert Msg4 "Please reflect a fingertip in the guide" as a notification reporting that no fingertip is detected, and outputs the generated alert Msg4 to the monitor 14 to be displayed thereon (St6A). The alert Msg4 may be output by voice. After the processing of step St6A, the processor 11 proceeds to the processing of step St3, and acquires a captured image from the camera 13 again.

Although not illustrated in the sequence diagram illustrated in FIG. 6, in the processing of step St2A, the user terminal device 1 may cut out an area including a selected fingertip and display the area on the monitor 14 in an enlarged manner. In addition, in the processing of step St2A, the user terminal device 1 may cut out an area including a selected position and display the area on the monitor 14 in an enlarged manner. Accordingly, the user can determine a finger to be used for fingerprint registration. In addition, since the user can determine a finger to be used for fingerprint registration after confirming a current state of the fingertip (for example, a scratched state, a stained state, or the like), it is possible to perform fingerprint registration more efficiently.

As described above, the fingerprint registration system 100 according to the second embodiment can display a guide on a captured image in a superimposed manner, and can indicate an imaging position to a user. Accordingly, the user can easily perform imaging to obtain a fingertip (fingerprint) image by positioning his/her hand so that a fingertip to be imaged is positioned in an area including a peripheral area of the guide Gu.

In addition, the fingerprint registration system 100 according to the second embodiment displays the guide indicating the imaging position of the fingertip in a superimposed manner in the imaging area of the camera 13. Accordingly, the fingerprint registration system 100 can easily detect the fingertip from the area including the peripheral area of the guide among the captured image captured by the camera 13, and also perform extraction of a feature of a fingerprint and generation of fingerprint data only for the fingerprint of the fingertip reflected in the detected area. Thus, it is possible to reduce a load in various types of processing required until the generation of the fingerprint data (that is, the fingerprint detection processing, the fingerprint feature extraction processing, the fingerprint data generation processing, and the like). Further, since the guide is displayed, the user can select a finger, of which a fingerprint thereof is desired to be registered, by performing imaging so that a fingertip of the finger desired for fingerprint registration is positioned in the area including the peripheral area of the guide, and the user can perform the registration while avoiding using a finger having a scratch or a finger whose skin is turned up. That is, since the user can determine a finger to be used for fingerprint registration after confirming a current state of the fingertip (for example, a scratched state, a stained state, or the like), it is possible to perform fingerprint registration more efficiently.

When no fingertip is detected from a periphery of the guide, the fingerprint registration system 100 according to the second embodiment outputs an alert indicating that no fingertip is present in the periphery of the guide. Accordingly, the fingerprint registration system 100 can notify the user that no fingertip is reflected in the area including the peripheral area of the guide.

Third Embodiment

The example is illustrated in which the fingerprint registration system 100 according to the second embodiment displays a guide indicating an imaging position of one fingertip for registering a fingerprint thereof in a superimposed manner, and detects a fingertip in an area including a peripheral area of the guide. With respect to the fingerprint registration system 100 according to a third embodiment, an example will be described in which a selection operation performed by a user for one finger registering a fingerprint is accepted and a fingertip of the selected finger is detected.

Figure 8:
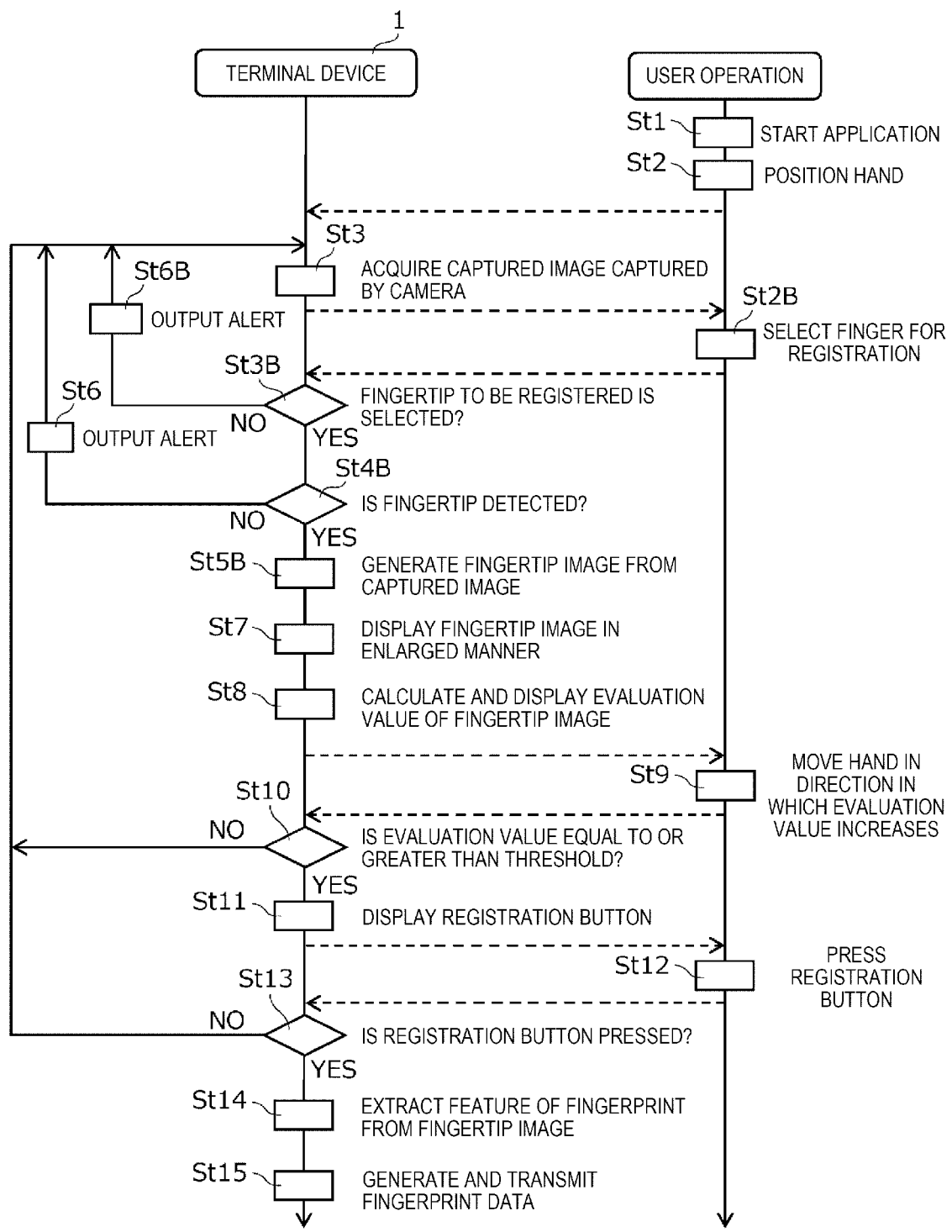
FIG. 8 is a sequence diagram illustrating an operation procedure and action procedure example of a user terminal device according to a third embodiment.
Figure 9:
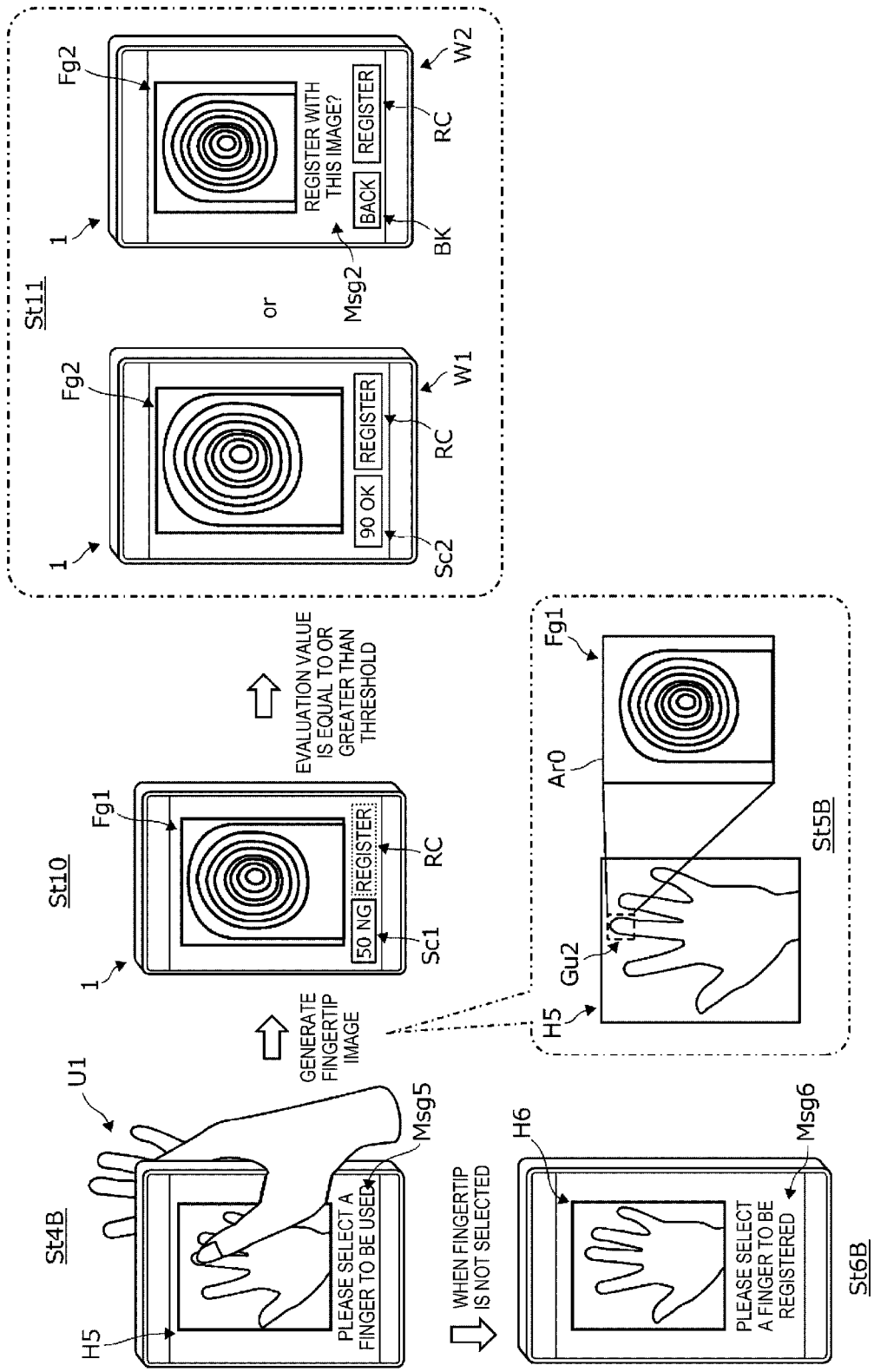
FIG. 9 is a diagram illustrating the operation procedure and action procedure example of the user terminal device according to the third embodiment.

An operation procedure and action procedure example of the user terminal device 1 according to the third embodiment will be described with reference to FIGS. 8 and 9. FIG. 8 is a sequence diagram illustrating the operation procedure and action procedure example of the user terminal device 1 according to the third embodiment. FIG. 9 is a diagram illustrating the operation procedure and action procedure example of the user terminal device 1 according to the third embodiment. In the example illustrated in FIG. 9, an evaluation value 80 of evaluation values 1 to 100 is set as a threshold. In steps St1 to St3, steps St7 to step St9, and steps St11 to St15 in the operation procedure and action procedure example of the user terminal device 1 according to the third embodiment, substantially the same processing as that in the operation procedure and action procedure example of the user terminal device 1 according to the first embodiment illustrated in FIG. 4 is executed. Therefore, the same operation procedures or action procedures as those in the first embodiment are denoted by the same reference signs, and a description thereof will be omitted.

In step St3, a user selects a finger for performing fingerprint registration on a captured image H5 displayed on the monitor 14 (St2B). Here, as in the example illustrated in step St4B illustrated in FIG. 9, the processor 11 may generate and display a message Msg5 "Please select a finger to be used" indicating an instruction for select a finger to be used for fingerprint registration. The message Msg5 may be output by voice.

The processor 11 determines whether one finger for registering a fingerprint is selected by the user (St3B). When there is a selection operation of a finger performed by the user in the processing of step St3B (St3B, YES), the processor 11 detects the selected finger by image analysis, and further detects a fingertip including at least a first joint of the selected finger (St4B).

On the other hand, when there is no selection operation of a finger performed by the user in the processing of step St3B (St3B, NO), the processor 11 generates an alert Msg6 "Please select a finger to be registered" as a notification that the selection operation of the finger to be registered is not detected, based on the input of the operation unit 15, as in the example illustrated in step St6B illustrated in FIG. 9, and outputs the generated alert Msg6 together with a captured image H6 to the monitor 14 to be displayed thereon (St6B). The alert Msg6 may be output by voice. After the processing of step St6B, the processor 11 proceeds to the processing of step St3, and acquires a captured image from the camera 13 again.

When the processor 11 detects a fingertip of the finger subjected to the selection operation of the user in the processing of step St4B (St4B, YES), the processor 11 cuts out the cutout area Ar0 including an imaging area including a detected fingertip Gu2 as in the example illustrated in step St5B in FIG. 9, and generates the fingertip image Fg1 (St5B).

On the other hand, when the fingertip of the finger subjected to the selection operation of the user is not detected in the processing of step St4B (St4B, NO), the processor 11 generates the alert Msg1 "Please reflect a fingertip" as a notification reporting that no fingertip is detected, and outputs the generated alert Msg1 to the monitor 14 to be displayed thereon (St6). The alert Msg1 may be output by voice. After the processing of step St6, the processor 11 proceeds to the processing of step St3, and acquires a captured image from the camera 13 again.

Although not illustrated in the sequence diagram illustrated in FIG. 8, in the processing of step St2B, the user terminal device 1 may cut out an area including the selected fingertip and display the area on the monitor 14 in an enlarged manner. In addition, in the processing of step St2B, the user terminal device 1 may cut out an area including a selected position and display the area on the monitor 14 in an enlarged manner. Accordingly, the user can intuitively determine (select) a finger to be used for fingerprint registration from among a plurality of fingers displayed on the monitor 14 having a function as a so-called touch panel.

As described above, the fingerprint registration system 100 according to the third embodiment can execute fingerprint registration of a finger subjected to a selection operation of a user. Accordingly, the user can perform fingerprint registration using a finger desired by the user, and can easily perform the fingerprint registration even when there is a finger that is not suitable for fingerprint registration due to injury or the like.

In addition, the fingerprint registration system 100 according to the third embodiment accepts a selection operation of the user for imaging one finger out of one or more fingers reflected in the imaging area of the camera, and images a fingertip of the finger selected by the selection operation. Accordingly, the fingerprint registration system 100 can support registration of fingerprint data based on a fingertip image captured so as to be suitable for fingerprint authentication. In addition, the user can intuitively determine (select) a finger to be used for fingerprint registration from among a plurality of fingers.

When there is no selection operation, the fingerprint registration system 100 according to the third embodiment outputs an alert indicating that one finger is not selected. Accordingly, the fingerprint registration system 100 can notify the user that no fingertip is reflected in an area including a peripheral area of a guide.

In addition, the fingerprint registration system 100 according to the third embodiment accepts a selection operation of the user for selecting one finger from among one or more fingers reflected in the imaging area of the camera, and displays the finger selected by the selection operation in an enlarged manner. Accordingly, the user can determine (select) a finger to be used for fingerprint registration according to a current state of the fingertip (for example, a scratched state, a stained state, or the like). In addition, since the user can determine a finger to be used for fingerprint registration after confirming a current state of the fingertip (for example, a scratched state, a stained state, or the like), it is possible to perform fingerprint registration more efficiently.

In addition, the fingerprint registration system 100 according to the third embodiment accepts a selection operation of the user with respect to an inside of the imaging area of the camera, and displays the position selected by the selection operation in an enlarged manner. Accordingly, the user can determine a finger to be used for fingerprint registration according to a current state of the fingertip (for example, a scratched state, a stained state, or the like). In addition, since the user can determine a finger to be used for fingerprint registration after confirming a current state of the fingertip (for example, a scratched state, a stained state, or the like), it is possible to perform fingerprint registration more efficiently.

Although various embodiments have been described above with reference to the accompanying drawings, the present disclosure is not limited to these embodiments. It will be apparent to those skilled in the art that various changes, modifications, substitutions, additions, deletions, and equivalents can be conceived within the scope of the claims, and it should be understood that such changes and the like also belong to the technical scope of the present disclosure. Components in the various embodiments described above may be combined freely within a range not departing from the gist of the invention.

The present application is based on Japanese Patent Application No. 2019-224796 filed on Dec. 12, 2019, and the contents thereof are incorporated herein by reference.

INDUSTRIAL APPLICABILITY

The present disclosure is useful as a fingerprint registration method and a user terminal device that support registration of fingerprint data based on a fingertip image captured so as to be suitable for fingerprint authentication.

REFERENCE SIGNS LIST 1 user terminal device
10, 20 communication unit
11, 21 processor
12, 22 memory
13 camera
14 monitor
15 operation unit
2 server
23 fingerprint database
Ar0 cutout area
Ar1 display area
Gu guide
Fg1, Fg2 fingertip image
Msg1, Msg4, Msg6 alert
RC registration button

The invention claimed is:

1. A fingerprint registration method to be executed by a user terminal device, the fingerprint registration method comprising:
   imaging a fingertip by a camera provided in the user terminal device;
   generating and displaying an enlarged image in which a fingertip image including an imaged fingertip is enlarged;
   accepting, based on the enlarged image, a user operation as to whether to register the fingertip image for fingerprint authentication;
   transmitting, as fingerprint data to an external server, the fingertip image subjected to a registration operation by the user operation,
   comparing an enlargement magnification in a longitudinal direction that is calculated based on a longitudinal width of the fingertip image and a longitudinal width of a display area of the user terminal device on which the enlarged image is displayed, and an enlargement magnification in a transverse direction that is calculated based on a transverse width of the fingertip image and a transverse width of the display area; and
   enlarging and generating the fingertip image by using a smaller enlargement magnification.

2. The fingerprint registration method according to claim 1,
   wherein the fingerprint data is data that is obtained by extracting, based on the fingertip image, a feature of a fingerprint for performing the fingerprint authentication.

3. The fingerprint registration method according to claim 1, further comprising:
   displaying, together with the enlarged image, a notification for requesting a user to visually confirm the enlarged image.

4. The fingerprint registration method according to claim 1, further comprising:
   calculating, based on the fingertip image, an evaluation value indicating whether a fingerprint reflected in the fingertip image is in focus; and
   displaying the calculated evaluation value together with the enlarged image.

5. The fingerprint registration method according to claim 1, further comprising:
   calculating, based on the fingertip image, an evaluation value indicating whether a fingerprint reflected in the fingertip image is in focus; and
   enabling acceptance of the registration operation when the evaluation value exceeds a threshold.

6. The fingerprint registration method according to claim 1, further comprising:
   calculating, based on the fingertip image, an evaluation value indicating whether a fingerprint reflected in the fingertip image is in focus;
   when the evaluation value does not exceed a threshold, regenerating a fingertip image and recalculating the evaluation value corresponding to the regenerated fingertip image; and
   repeating regeneration of the fingertip image and recalculation of the evaluation value based on the regenerated fingertip image until the recalculated evaluation value exceeds the threshold.

7. The fingerprint registration method according to claim 1, further comprising:
   imaging the fingertip based on an imaging operation of a user.

8. The fingerprint registration method according to claim 1, further comprising:
   after transmitting the fingerprint data, deleting the fingertip image subjected to the registration operation from the user terminal device.

9. The fingerprint registration method according to claim 1, further comprising:
   when the fingertip is not reflected in an imaging area of the camera, outputting an alert indicating that the fingertip is not present in the imaging area.

10. The fingerprint registration method according to claim 1, further comprising:
    displaying a guide for indicating an imaging position of the fingertip, in an imaging area of the camera in a superimposed manner.

11. The fingerprint registration method according to claim 10, further comprising:
    when the fingertip is not detected from a periphery of the guide, outputting an alert indicating that the fingertip is not present in the periphery of the guide.

12. The fingerprint registration method according to claim 1, further comprising:
    accepting a selection operation of a user for imaging one finger out of one or more fingers reflected in an imaging area of the camera.

13. The fingerprint registration method according to claim 12, further comprising:
    when the selection operation is not performed, outputting an alert indicating that the one finger is not selected.

14. The fingerprint registration method according to claim 12, further comprising:
    accepting the selection operation of the user for selecting one finger from among the one or more fingers reflected in the imaging area of the camera; and
    displaying the finger selected by the selection operation in an enlarged manner.

15. The fingerprint registration method according to claim 1, further comprising:
    accepting a selection operation of a user with respect to an inside of an imaging area of the camera; and
    displaying a position selected by the selection operation in an enlarged manner.

16. A user terminal device communicably connected to an external server, the user terminal device comprising:
- a camera that is configured to image a fingertip;
- a processor that is configured to generate an enlarged image in which a fingertip image including the fingertip captured by the camera is enlarged;
- a monitor that is configured to display the generated enlarged image;
- an operation unit that is configured to accept a user operation as to whether to register the fingertip image for fingerprint authentication; and
- a communication unit that is configured to transmit, as fingerprint data to the external server, the fingertip image registered by the user operation, wherein
- the processor compares an enlargement magnification in a longitudinal direction that is calculated based on a longitudinal width of the fingertip image and a longitudinal width of a display area of the user terminal device on which the enlarged image is displayed, and an enlargement magnification in a transverse direction that is calculated based on a transverse width of the fingertip image and a transverse width of the display area, and
- the processor enlarges and generates the fingertip image by using a smaller enlargement magnification.

* * * * *